United States Patent
Watson et al.

(10) Patent No.: US 9,236,046 B2
(45) Date of Patent: Jan. 12, 2016

(54) SYSTEMS AND METHODS FOR IDENTIFYING PATIENT DISTRESS BASED ON A SOUND SIGNAL

(71) Applicant: Covidien LP, Mansfield, MA (US)

(72) Inventors: James Nicholas Watson, Dunfermline (GB); Paul Stanley Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 215 days.

(21) Appl. No.: 13/829,068

(22) Filed: Mar. 14, 2013

(65) Prior Publication Data

US 2014/0278388 A1    Sep. 18, 2014

(51) Int. Cl.
| | |
|---|---|
| A61B 5/0205 | (2006.01) |
| G10L 15/00 | (2013.01) |
| A61B 7/00 | (2006.01) |
| G10L 25/63 | (2013.01) |
| A61B 5/00 | (2006.01) |
| A61B 5/021 | (2006.01) |
| A61B 5/024 | (2006.01) |
| A61B 5/08 | (2006.01) |

(52) U.S. Cl.
CPC .................. *G10L 15/00* (2013.01); *A61B 7/003* (2013.01); *G10L 25/63* (2013.01); *A61B 5/021* (2013.01); *A61B 5/02416* (2013.01); *A61B 5/0816* (2013.01); *A61B 5/743* (2013.01)

(58) Field of Classification Search
CPC ......... G10L 25/63; G10L 15/00; G10L 15/12; G10L 15/08; G10L 15/10; A61B 7/003; A61B 5/743; A61B 5/02416; A61B 5/0816; A61B 5/021; A61B 5/0022; A61B 5/0205

USPC .......... 704/231, 246, 270, 239; 600/493, 300, 600/364, 484, 508, 509; 340/573.1, 3.1, 340/539.13, 6.1, 321, 384.1; 379/106.02, 379/38; 434/272, 262
See application file for complete search history.

(56) References Cited

U.S. PATENT DOCUMENTS

| | | | | |
|---|---|---|---|---|
| 4,810,996 | A * | 3/1989 | Glen et al. | 340/321 |
| 5,309,921 | A * | 5/1994 | Kisner et al. | 600/532 |
| 5,601,435 | A * | 2/1997 | Quy | 434/307 R |
| 6,028,514 | A * | 2/2000 | Lemelson et al. | 340/539.13 |
| 6,083,163 | A * | 7/2000 | Wegner et al. | 600/429 |
| 6,129,675 | A | 10/2000 | Jay | |
| 6,238,354 | B1 * | 5/2001 | Alvarez | 600/549 |
| 6,325,761 | B1 | 12/2001 | Jay | |
| 7,407,485 | B2 | 8/2008 | Huiku | |
| 7,558,622 | B2 * | 7/2009 | Tran | 600/509 |
| 8,441,356 | B1 * | 5/2013 | Tedesco et al. | 340/573.1 |
| 2004/0015091 | A1 | 1/2004 | Greenwald et al. | |
| 2005/0062588 | A1 * | 3/2005 | Spector | 340/3.1 |
| 2006/0241510 | A1 * | 10/2006 | Halperin et al. | 600/534 |

(Continued)

FOREIGN PATENT DOCUMENTS

WO          03084396 A1     3/2013

*Primary Examiner* — Vijay B Chawan
(74) *Attorney, Agent, or Firm* — Shvarts & Leiz LLP

(57) ABSTRACT

A sound signal from a patient may include information that may be used to determine multiple patient parameters. A patient monitor may determine respiration information such as respiration rate from the sound signal, for example based on modulations of the sound signal due to patient breathing. The patient monitor may also determine indications of patient distress based on a trained classifier, speech commands, or sound patterns.

20 Claims, 5 Drawing Sheets

(56) References Cited

U.S. PATENT DOCUMENTS

| | | |
|---|---|---|
| 2007/0276270 A1* | 11/2007 | Tran .............................. 600/508 |
| 2008/0064965 A1 | 3/2008 | Jay et al. |
| 2008/0081956 A1 | 4/2008 | Shah et al. |
| 2012/0092157 A1* | 4/2012 | Tran ......................... 340/539.12 |
| 2012/0123223 A1* | 5/2012 | Freeman et al. ............... 600/301 |
| 2013/0197322 A1* | 8/2013 | Tran .............................. 600/301 |

* cited by examiner

SYSTEMS AND METHODS FOR IDENTIFYING PATIENT DISTRESS BASED ON A SOUND SIGNAL

The present disclosure relates to physiological signal processing, and more particularly relates to identifying patient distress based on a sound signal.

SUMMARY

A method comprises receiving a sound signal from a sensor that senses sound from a patient, computing, with processing equipment, one or more metrics based on the sound signal, determining, with the processing equipment, a classification of the sound signal based on the one or more metrics and on a classifier, wherein the classifier is trained based on signal characteristics that correspond to patient distress, determining, with the processing equipment, whether the sound signal corresponds to patient distress based on the classification, and outputting an indication of patient distress when patient distress is determined to be present.

A non-transitory computer-readable storage medium for processing a sound signal has computer program instructions recorded thereon for receiving a sound signal from a sensor that senses sound from a patient, computing one or more metrics based on the sound signal, determining a classification of the sound signal based on the one or more metrics and on a classifier, wherein the classifier is trained based on signal characteristics that correspond to patient distress, determining whether the sound signal corresponds to patient distress based on the classification, and outputting an indication of patient distress when patient distress is determined to be present.

A monitoring unit comprises processing equipment configured to receive a sound signal from a sensor that senses sound from a patient, compute one or more metrics based on the sound signal, determine a classification of the sound signal based on the one or more metrics and on a classifier, wherein the classifier is trained based on signal characteristics that correspond to patient distress, determine whether the sound signal corresponds to patient distress based on the classification, and output an indication of patient distress when patient distress is determined to be present.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

In a medical setting a patient may convey information to medical professionals verbally through speech. In addition, significant information may also be conveyed based on the tone, level, pitch, and patterns of the patient's speech, as well as other sounds (e.g., groans, screams, heavy breathing, and abrupt changes in level or pitch). Further, it may be possible to determine physiological parameters based on patient speech and other sounds, including information related to patient breathing such as respiration rate.

In some embodiments, of the present disclosure, a microphone may receive a sound signal based on sound emanating from a patient into a microphone or other sound-sensitive device. The sound signal from the microphone may be transmitted to a monitoring unit. The monitoring unit may utilize different aspects of the sound signal for patient monitoring, including to determine respiration rate, identify patient distress, and make other determinations regarding the patient. For example, patient distress may be determined in a number of different manners, such as based on speech commands, analysis of non-speech sounds, based on analysis of the sound signal by a classifier, or any combination thereof.

For purposes of brevity and clarity, the present disclosure is written in the context of receiving a sound signal based on sound emanating from a patient into a microphone or other sound-sensitive sensor, determining respiration information such as respiration rate from the sound signal, and identifying indications of patient distress from the sound signal. It will be understood that any suitable physiological signal (e.g., photoplethysmograph (PPG), blood pressure, patient air flow, any other suitable signal, or any combination thereof) may be used in place of or in addition to the sound signal in accordance with the teachings of the present disclosure. It will also be understood that any other suitable physiological parameter may be determined in place of or in addition to respiration rate, or that an identification of patient distress may be performed in accordance with the teachings of the present disclosure without also determining additional physiological parameters.

For purposes of brevity and clarity, the present disclosure refers to patient distress. Patient distress may be indicative of any suitable type of patient distress, conditions likely to result in patient distress, and indirect indications of patient distress, and includes patient inconvenience, physical distress, mental distress, physical pain, abnormal values of patient physical parameters, low quantities of medical supplies, requests for treatment, any other suitable indication of patient distress, or any combination thereof.

Figure 1:
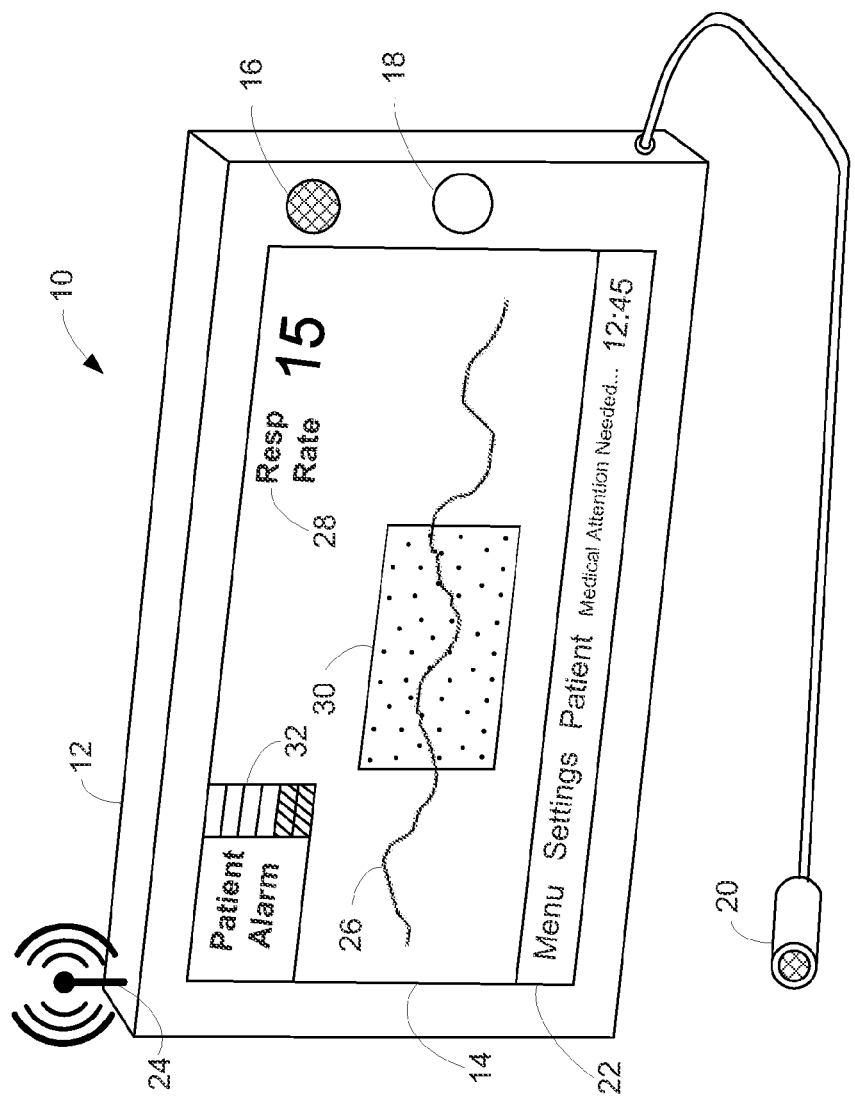
FIG. 1 shows an illustrative patient monitoring system in accordance with some embodiments of the present disclosure.

FIG. 1 is a perspective view of an am embodiment of a patient monitoring system 10. System 10 may include monitoring unit 12 and microphone 20. Monitoring unit 12 may provide for any suitable functionality, including user interface, data communications, interface with physiological sensors such as microphone 20, any other suitable functionality, or any combination thereof. Although a particular configuration of monitoring unit 12 is described herein it will be understood that monitoring unit 12 may be implemented in any suitable manner.

In some embodiments, monitoring unit 12 may be implemented on a tablet-type computer unit, including a display 14, speaker 16, power/wake button 18, and communication interface 24. It will be understood that any suitable device including suitable user interface, display, data inputs, and communication interfaces may be utilized in accordance with the present disclosure. In some embodiments, a personal computer, smart phone, or other standard computing device may implement the systems and methods described herein. In some embodiments, the systems and methods described herein may be implemented in a custom patient monitor, for example, to implement the specific functionality described herein or in combination with other patient monitoring functions.

As is described herein, monitoring unit 12 may analyze physiological information such as sound information received from microphone 20 to identify respiration information such as respiration rate and conditions such as patient distress. In some embodiments, a time series of respiration data related to inhalation and exhalation may be obtained and stored at monitoring unit 12. Although the respiration information may be determined from the respiration data in any suitable manner, in some embodiments, respiration information may be determined directly (e.g., by identifying sounds related to exhalation and inhalation), indirectly (e.g., by identifying changes in audible sounds due to respiration), in any other suitable manner, or any combination thereof. As is described herein, monitoring unit 12 may identify patient distress based on patient speech (e.g., patient commands), patient sounds (e.g., screams, lengthy groans, or abrupt changes in speech or breathing), or a trained classifier (e.g., a classifier that identifies patient distress based on training information such as sound patterns that conform to patient distress, patient speech and sound characteristics, or any combination thereof).

Although a microphone is described herein, it will be understood that any other suitable sensor or combination of sensors may be used in place of or in addition to microphone 20 in accordance with the embodiments described herein. For example, in some embodiments, respiration information such as respiration rate may be determined by one or more additional sensors in combination with or in place of microphone 20. Exemplary sensors may produce capnography signals, plethysmograph signals, trans-thoracic impedance signals, flow signals, thermistor signals, displacement signals (e.g., from chest or abdomen bands), any other suitable signals, or any combination thereof.

In some embodiments, display 14 may provide a touch screen interface for users of monitoring unit 12. Although display 14 may be configured in any suitable manner, in some embodiments, display 14 may include menu 22, respiration waveform 26, respiration rate portion 28, alarm window 30, and patient alarm portion 32. Although monitoring unit 12 may be configured to determine any suitable physiological parameters based on any suitable sensor or data inputs, in some embodiments, monitoring unit 12 may calculate respiration rate based on information received from microphone 20. In some embodiments, respiration rate may be calculated at microphone 20, at an intermediate processing unit (not depicted), or at a remote processing unit (e.g., a remote computer or server) accessed via a communication link established by communication interface 24.

Microphone 20 may be any suitable microphone or combination of microphones that generates an electrical signal based on sounds received from a patient. Although microphone 20 is depicted as being physically coupled to monitor, it will be understood that electrical signals from microphone 20 may be transmitted to monitoring unit 12 in any suitable manner. In some embodiments, signals from microphone 20 may be transmitted wirelessly to an audio receiver of monitoring unit 12 (not depicted), converted to digital data and transmitted using standard communications protocols to monitoring unit 12 (e.g., via communication interface 24) (not depicted), or transmitted in any other suitable manner.

Microphone 20 may be located at any suitable location relative to a patient. In some embodiments, microphone 20 may be located in a manner such that it is capable of receiving sounds related to patient airflow in addition to audible speech and noises. In some embodiments, microphone 20 may be configured to receive a range of sounds including human speech, sounds that are directly indicative of respiration (e.g., airflow from breathing), cardiac sounds, modulations of speech or other human sounds caused by respiration, sounds caused by patient distress, any other suitable sounds, or any combination thereof. Patient distress may be indicated by any suitable sounds, combination of sounds, series of sounds over time, any other suitable sound patterns, or any combination thereof. In some embodiments, indications of patient distress may include groans, grunts, screams, sharp intakes of breath, abrupt changes in the pitch or volume of speech or other sounds, speech commands, any other suitable sounds and sound patterns that are indicative of patient distress, or any combination thereof.

In some embodiments, respiration waveform 26 may be a waveform that is indicative of a patient's inhalation and exhalation as determined by monitoring unit 12. Respiration waveform 26 may be scaled in any suitable manner (e.g., based on selections of menu 22) for display, and may display real time data, stored respiration waveforms or other stored respiration information (e.g., a time-trend of respiration rate measurements) stored within memory of monitoring unit 12, or any other suitable information relating to respiration. It will also be understood that information relating to any other suitable physiological parameters may be displayed as a waveform in place of or in addition to respiration waveform 26.

Although any suitable physiological parameters may be displayed in accordance with the present disclosure, in some embodiments, a patient's respiration rate may be displayed at respiration rate display portion 28. Although a physiological parameter such as respiration rate may be displayed in any suitable manner, in some embodiments, a value for the respiration rate may be displayed in breaths per minute, and the respiration rate portion 28 may flash when the calculated respiration rate falls outside of one or more predetermined limits (not depicted) which may be set, for example, by accessing menu 22. Although predetermined limit violations may be determined in any suitable manner, in exemplary embodiments the respiration rate limit may include an upper and lower limit. In some embodiments, an alarm may be set to sound based on the degree of the respiration rate violation, based on the duration of the respiration rate violation, based on the rate of change of respiration rate, based on any other suitable parameters, or any combination thereof.

In some embodiments, patient alarm portion 32 may display an alarm when an indication of patient distress has been identified in accordance with some embodiments of the present disclosure. Although a patient alarm indicative of patient distress may be displayed in patient alarm portion in any suitable manner, in some embodiments, a patient alarm may be indicated by flashing a portion of the screen, an alphanumeric alarm display, one or more icons, a severity indicator, any other suitable indicator, or any combination thereof. In some embodiments, different types of alarms relating to patient distress may be indicated by different alphanumeric displays, alarm colors, icons, or any combination thereof.

In some embodiments, alarm window 30 may overlay respiration waveform 26 to provide an indication of when an alarm occurs relative to respiration waveform 26. Although any suitable alarms may be indicated by alarm window 30 in this manner in accordance with the present disclosure, in some embodiments, alarm window 30 may appear when the respiration rate falls outside of predetermined limits or when patient distress has been identified. In some embodiments, alarm window 30 may be displayed with respiration waveform 26 for recently received data, as well as for any respiration waveform 26 for stored respiration waveform data or respiration trend data (e.g., stored respiration rate trend data). Although alarm window 30 may be displayed in any suitable manner, in some embodiments, alarm window 30 may be a shaded area that overlays the portion of respiration waveform 26 that is associated with the alarm. In some embodiments, different alarm types (e.g., respiration rate upper limit alarms, respiration rate lower limit alarms, and indications of patient distress) may be indicated in different manners, such as by changing the color of alarm window 30. Although multiple alarm types may be displayed simultaneously in any suitable manner, in some embodiments, any portion of alarm window 30 that is associated with multiple alarms may display both alarm colors simultaneously, for example, as interspersed colored bars within alarm window 30 (not depicted).

In some embodiments, menu portion 22 may include menus that allow a user to input data, adjust settings, change views, or interact with monitoring unit 12 in any suitable manner. In some embodiments, menu portion 22 may be implemented on display 14, although it will be understood that menu portion 22 may be implemented in any suitable manner based on available user input options (e.g., buttons, keyboard, mouse, track pad, voice recognition, any other suitable user input, or any combination thereof) and display type of monitoring unit 12. Although menu portion 22 may include any suitable menus or information, in some embodiments, menu portion 22 may include selectable menus for "menu," "settings," and "patient," an informational area that includes messages to users (e.g., alarm information, help menus, and status information), and information such as time and date. The selectable menus of menu portion 22 may allow a user to adjust any suitable parameters and perform any suitable tasks for monitoring unit 12. Although any suitable functionality may be implemented by menu portion 22, in exemplary embodiments a user may be able to modify patient information, adjust alarm limits, define parameters to be measured, view or download stored data, and communicate with other devices (e.g., via voice, video, e-mail, or text messaging). In some embodiments, the options available through menu portion 22 may be based at least in part on a user's login credentials.

Although speaker 16 may be utilized in any suitable manner, in some embodiments, speaker 16 may provide audible sounds from monitoring unit 12 to enable monitoring unit 12 to communicate with patients or medical professionals and enable a user to communicate with other communication devices or users at other communication devices, nurse stations, mobile telephones, or any other suitable communication device. In some embodiments, speaker 16 may provide audible tones or messages in response to alarms or indications of patient distress determined by monitoring unit 12. In some embodiments, the pitch, sound level, and duration of an alarm may be modified based on alarm type, alarm duration, alarm severity, any other suitable parameter related to alarms or the patient, or any combination thereof. In some embodiments, speaker 16 may provide spoken messages to a user, such as synthesized speech or prerecorded messages associated with alarms, indications of patient distress, and user inputs.

In some embodiments, communication interface 24 may provide for communication with devices external to monitoring unit 12. Although any suitable communication technologies may be implemented by communication interface 24, in some embodiments, communication interface 24 may include wired technologies (e.g., Ethernet, USB, FireWire, SCSI, and fiber networks), wireless technologies (e.g., WiFi, 3G networks, 4G networks, infrared, and radio frequency links), any other suitable communication technologies, or any combination thereof. It will be understood that any suitable communications with any suitable external devices may be performed via communication interface 24, such as data downloads, exchange of patient information, audio communications, video conferencing, and communication with other patient monitors and nurse stations.

Figure 2:
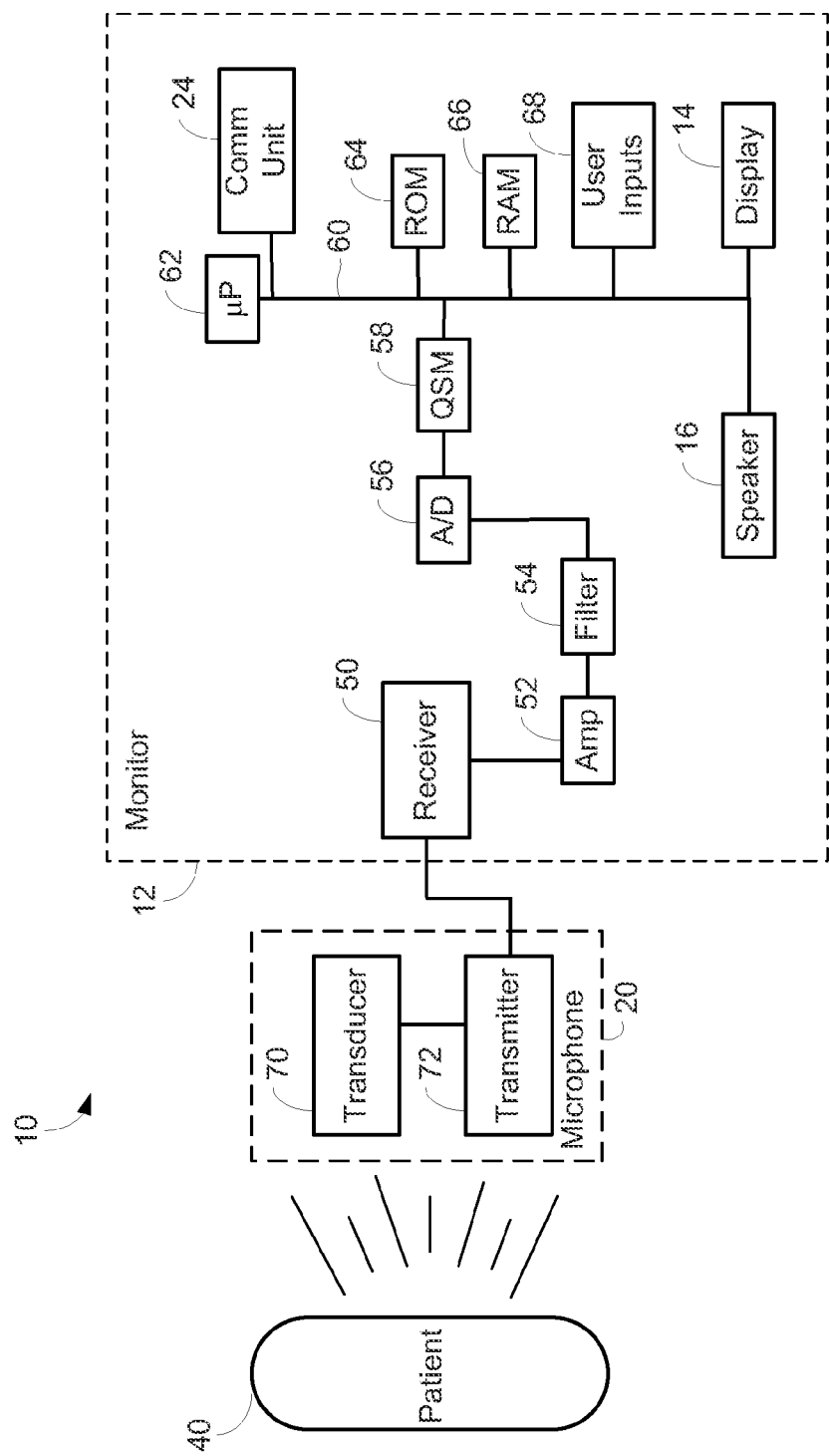
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment of the present disclosure. Although this disclosure will be described with respect to a microphone measuring a sound signal, it will be understood that any suitable physiological measurement device may measure any suitable parameters in accordance with the present disclosure. Certain illustrative components of microphone 20 and monitoring unit 12 are illustrated in FIG. 2. Any suitable combination of components may be referred to herein as "processing equipment."

Microphone 20 may include transducer 70 and transmitter 72. Microphone 20 may be connected to a power source, for example via a wired connection with monitoring unit 12, or with an internal power source such as a battery (e.g., for a wireless microphone (not depicted)). It will be understood that microphone 20 may be any suitable microphone type based on any suitable transducer 70 type, such as condenser microphones, dynamic microphones, electret microphones, piezoelectric microphones, fiber optic microphones, laser microphones, micro electrical mechanical system (MEMS) microphones, any other suitable microphone, or any combination thereof. In some embodiments, multiple microphones 20, multiple transducer 70 types, or any combination thereof, may be selected to better identify different sound profiles (e.g., speech, respiration, or indications of patient distress). Each transducer 70 may generate an electrical signal based on sound received at microphone 20, and an associated transmitter 72 may transmit the electrical signal output by transducer 70 to monitoring unit 12.

In some embodiments, one or more of the components described below with respect to monitoring unit 12 (e.g., amplifier 52, filter 54, A/D converter 56, any other suitable component, or any combination thereof) may be located at microphone 20. In this manner, the sound information received at transducer 70 may be processed or partially processed prior to being transmitted by transmitter 72 to receiver 50 of monitoring unit 12. In some embodiments, microphone 20 may include a processor and memory (not depicted) to perform data processing and transmitting functions (including some or all of amplifier 52, filter 54, A/D converter 56, any other suitable component, or any combination thereof). Although any suitable processing may be implemented at microphone 20, in some embodiments, sound signals converted to electrical signals by transducer 70 and processed (e.g., by amplifier 52, filter 54, A/D converter 56, any other suitable component, or any combination thereof) may be converted into digital data for transmission to monitoring unit 12. Although sound information may be converted into digital data in any suitable manner, in some embodiments, audio codecs, speech codecs, any other suitable sound processing technique, or any combination thereof, may be used to convert electrical sound information (e.g., due to speech, respiration, or indications of distress) into digital data.

Signals from microphone 20 may be transmitted by transmitter 72 to a receiver 50 of monitoring unit 12. Although receiver 50 may receive any suitable sound signal in any suitable form, in some embodiments, the received signal may be an electrical signal produced by transducer 70 of microphone 20 or digital data representing a sound signal. In some embodiments, receiver 50 or a plurality of receivers 50 may receive a plurality of signals associated with different sound profiles (e.g., due to respiration, speech, or indications of patient distress) for independent or combined processing in accordance with the present disclosure.

In the embodiment shown, monitoring unit 12 may include a general-purpose microprocessor 62 connected to an internal bus 60. Microprocessor 62 may be adapted to execute software, which may include an operating system and one or more applications, as part of performing the functions described herein. Also connected to bus 60 may be a read-only memory (ROM) 64, a random access memory (RAM) 66, user inputs 68, display 20, communication interface 24, and speaker 16.

RAM 66 and ROM 64 are illustrated by way of example, and not limitation. Any suitable computer-readable media may be used in the system for data storage. Computer-readable media are capable of storing information that can be interpreted by microprocessor 62. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In some embodiments, the received signal from receiver 50 may be processed by amplifier 52, filter 54, and analog-to-digital converter 56. The digital data may then be stored in QSM 58 (or buffer) for later downloading to RAM 66 as QSM 58 is filled. In some embodiments, there may be multiple separate parallel paths for multiple received signals including additional components such as to amplifier 52, filter 54, and/or A/D converter 56.

In some embodiments, microprocessor 62 may determine respiration information from aspects of the sound signal relating to respiration. Respiration information may include respiration rate, which may be determined using various algorithms and/or look-up tables based on values calculated from the received signals and/or data corresponding to the signal or data received by receiver 50. Microprocessor 62 may generate a time series (trend) of respiration rate data from determined respiration rate values.

In some embodiments, microprocessor 62 may identify words, phrases, sounds, or any combination thereof in order to identify user requests, commands, indications of patient distress, or any other suitable information. Speech information may be identified in any suitable manner, including any suitable speech recognition technique.

In some embodiments, microprocessor 62 may identify indications of patient distress. Indications of patient distress may be determined based on respiration information (e.g., breathing patterns related to patient distress), speech information (e.g., commands, requests, or phrases indicating distress), sounds (e.g., screams, groans, sharp intakes of breath, abrupt changes in breathing patterns), any other suitable received data, or any combination thereof. In some embodiments, patient distress may be identified directly, for example based on particular commands, sounds, or breathing patterns. In some embodiments, patient distress may be identified by a trained classifier implemented by monitoring unit 12 as described herein.

Although any suitable classifier may be used in accordance with the present disclosure, exemplary classifiers may include neural networks (e.g., maximum partial likelihood (MPL) networks or radial basis networks), genetic algorithms, stochastic and probabilistic classifiers (e.g., Basian, HMM, or fuzzy classifiers), propositional or predicate logics (e.g., non-monotonic or modal logics), nearest neighbor classification methods (e.g., $k^{th}$ nearest neighbor or learning vector quantization (LVQ) methods), any other suitable classifiers, or any combination thereof. Although any suitable signal processing techniques may be employed by the classifiers, exemplary signal processing techniques may include principal component analysis (PCA), independent component analysis (ICA), linear discriminate analysis (LDA), fast Fourier transforms, continuous wavelet transforms, Hilbert transforms, Laplace transforms, any other suitable signal processing method, or any combination thereof.

A classifier may be trained based on any suitable input parameters such as speech, sounds, respiration patterns, or any combination thereof. Training data may be any suitable data such as example data from a particular patient or a group of patients that have been determined to have experienced patient distress conditions. Any portion of the training for the classifier may be performed at any suitable device at any suitable time. In some embodiments, the classifier may be trained entirely external to monitoring unit 12 and the classifier parameters may be stored at monitoring unit 12. In some embodiments, some or all of the training of the classifier may be performed at monitoring unit 12. For example, in some embodiments, parameters of the classifier may be updated for each patient. In some embodiments, the classifier may be continuously or periodically updated based on data received by monitoring unit 12 or by a number of monitoring units 12 (e.g., at a central monitoring station).

Although received data from a patient being monitored may be analyzed by a trained classifier in any suitable manner, in some embodiments, one or more metrics may be determined based on sound data, respiration information, speech, any other suitable physiological parameter, or any combination thereof. As is described herein, the metrics may then be input to the classifier to output a classification. Any suitable classifications may be provided in accordance with the present disclosure, including classifications related to patient distress. In some embodiments, one or more classifications related to patient distress may indicate the severity of the patient distress.

In some embodiments, user inputs 68 may be used to enter information, select one or more options, provide a response, input settings, perform any other suitable input function, or any combination thereof. User inputs 68 may be used to enter information about the patient, such as age, weight, height, diagnosis, medications, treatments, and so forth. In some embodiments, display 14 may display values, data, alarms, menus, user messages, any other suitable information, or any combination thereof.

Communication interface 24 may provide for communication with other devices utilizing any suitable transmission medium as described herein. Communication interface 24 may receive messages to be transmitted from microprocessor 62 via bus 60. Exemplary data to be communicated may include respiration rate data, trend data, alarm information, indications of patient distress, speech signals, video signals, any other suitable information, or any combination thereof. In some embodiments, calculated metrics may be transmitted to an external device for determining one or more classifications based on determined metrics.

Figure 3:
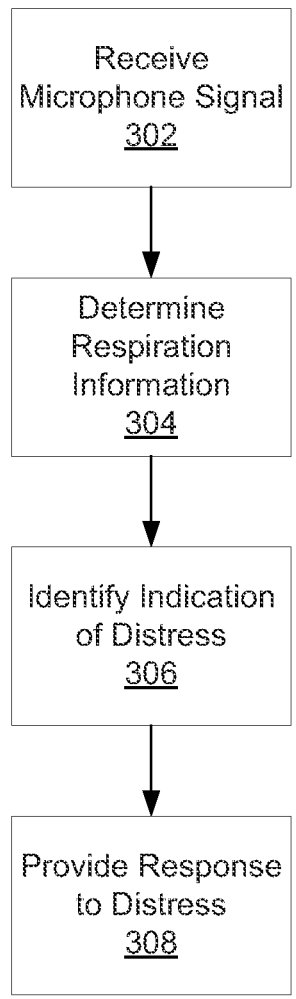
FIG. 3 shows illustrative steps for determining respiration information and identifying distress of a patient in accordance with some embodiments of the present disclosure.

FIG. 3 is a flow diagram showing illustrative steps for determining respiration information and identifying distress of a patient in accordance with some embodiments of the present disclosure. In some embodiments, the steps described in FIGS. 3-5 figures may be performed by system 10. However, it will be understood that some or all of the steps of FIGS. 3-5 may be performed by one or more other devices such as a remote or networked patient monitor or central monitoring station.

At step 302, one or more microphones may generate a sound signal based on sound emanated by a patient. Although any suitable sound signal may be generated by any suitable microphone or microphones, in some embodiments, microphone 20 may include two transducers 70, with a first transducer configured to receive (higher frequency) speech and voice sounds and a second transducer configured to receive (lower frequency) respiratory sounds. First and second sound signals may be transmitted by transmitters 72 of microphone 40 to receivers 50 of monitoring unit 12. Although the received signals may be processed in any suitable manner, in some embodiments, each of the received signals may be processed by an amplifier 52 and filter 54 tuned to isolate and identify the desired sounds associated with each signal (e.g., speech or respiration) before processing by A/D converter 56 and QSM 58, and storage at RAM 66 for processing by processor 62.

At step 304, processor 62 of monitoring unit 12 may determine respiration information such as respiration rate based on a received sound signal. Although respiration rate may be determined in any suitable manner, in some embodiments, respiration rate may be determined in accordance with the steps of FIG. 4.

Figure 4:
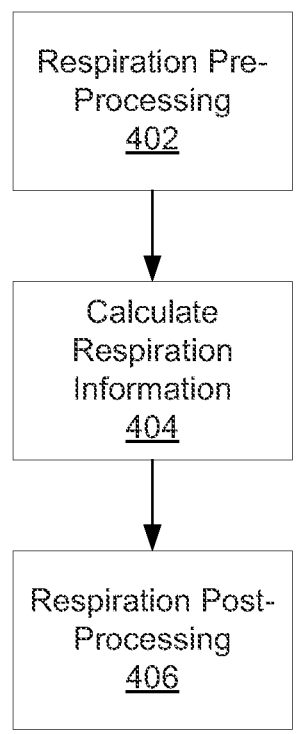
FIG. 4 shows illustrative steps for determining respiration information in accordance with some embodiments of the present disclosure.
Figure 5:
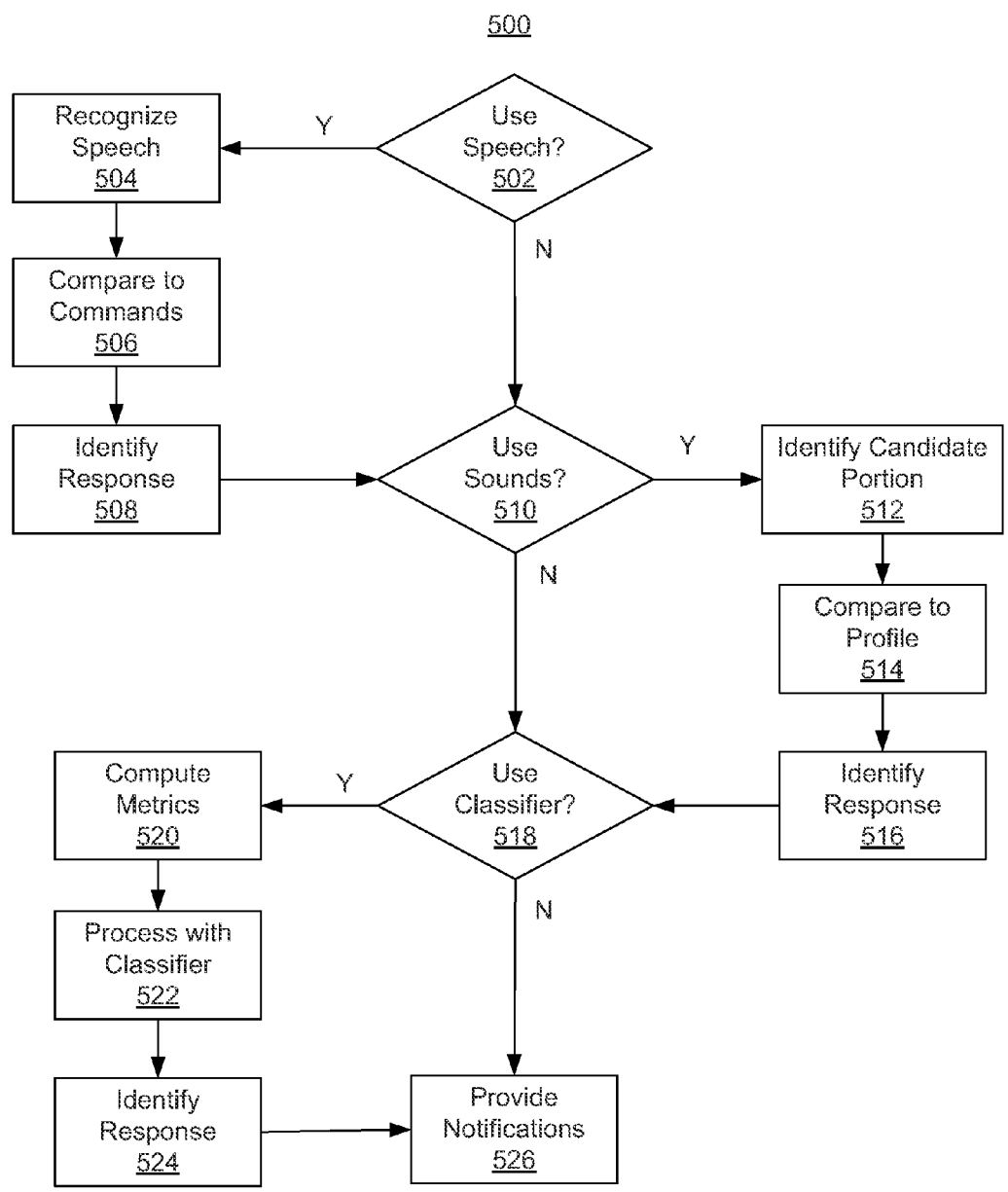
FIG. 5 shows illustrative steps for identifying patient distress in accordance with some embodiments of the present disclosure.

FIG. 4 shows illustrative steps for determining respiration information in accordance with some embodiments of the present disclosure. Although it will be understood that respiration information may be calculated from any suitable signal or combination of signals (e.g., blood pressure signal, photoplethysmograph signal, air flow signal, motion signal (e.g., from measurements of body motion due to respiration), microphone (sound) signal, any other suitable signal, or any combination thereof), in some embodiments, respiration information may be calculated based on a sound signal from microphone 20. Although any suitable techniques may be performed to determine respiration information, in exemplary embodiments monitoring unit 12 may perform respiration pre-processing, calculate respiration information, perform respiration post-processing, and communicate respiration information.

At step 402, processor 62 may perform respiration pre-processing on the received sound signal to generate a respiration signal. Although any suitable pre-processing techniques may be involved in respiration pre-processing, in some embodiments, respiration pre-processing may distinguish between portions of the sound signal that are likely to reflect data that is related to respiration and portions of the sound signal that are likely to reflect other information unrelated to respiration information, such as measurement error or signal noise. For example, microphone 20 may be moved, temporarily located at a location remote from the desired location, or may encounter some other form of interference that degrades the signal or otherwise interferes with the identification of respiration information from the sound signal. In some embodiments, pre-processing may identify portions of the sound signal that fall outside of an acceptable value range for frequency, signal intensity, respiration rate, any other suitable parameter, or any combination thereof. Any portion of the sound signal that is identified may be compensated for in any suitable manner, for example, by excluding the data associated with the portion of the signal from determination of respiration information, down-weighting the data, or supplementing the data with respiration information available from other sources (e.g., based on modulations to a sound signal associated with speech or based on respiration signals determined from other measurement sources). In some embodiments, the received sound signal for determining respiration information may be the same received sound signal for determining speech information (e.g., in an embodiment with a single received sound signal), and pre-processing for respiration may include filtering, for example, to emphasize sounds that are associated with respiration.

At step 404, processor 62 may calculate respiration information based on the pre-processed respiration signal. Although any suitable respiration information may be determined, in some embodiments, the respiration information may be respiration rate. Although respiration rate may be determined in any suitable manner, in some embodiments, the pre-processed respiration signal may be analyzed over time to determine a rolling average of a respiration rate. In some embodiments, a time series of respiration data from the pre-processed respiration signal may be analyzed to identify periodic aspects of the respiration signal, for example based on a Fourier transform, wavelet transform, performing an autocorrelation of the pre-processed respiration signal and identifying a period associated with a peak of the autocorrelation sequence, any other suitable technique for identifying periodic respiration information, or any combination thereof.

At step 406, processor 62 may perform post-processing based on the determined respiration rate. Although any suitable post-processing may be performed, in some embodiments, the currently determined respiration rate may be combined with one or more recently determined respiration rates to determine a rolling average. In some embodiments, the averaging may be weighted based on a confidence value for the recently determined respiration rate. Although a confidence value may be determined in any suitable manner, in some embodiments, the confidence value may be based on the percentage of the respiration signal that was determined to include respiration information in pre-processing step 402, signal strength, a comparison of the most recently determined respiration rate value to previous respiration rate values, any other suitable measurement or determination, or any combination thereof. The result of the post-processing may be a respiration rate value, for example, for display and storage at monitoring unit 12.

Returning to FIG. 3, at step 306, processor 62 may identify an indication of patient distress. Although an indication of patient distress may be identified based on any suitable signal or combination of signals, in some embodiments, an identification of distress may be identified based on a sound signal received at microphone 20. In some embodiments, processing to identify patient distress may be performed in accordance with the steps depicted in FIG. 5.

At step 502, processor 62 may determine whether to use speech from the sound signal to identify patient distress. Although the determination of whether to use speech may be performed in any suitable manner, in some embodiments, the determination may be based on the settings for monitoring unit 12, a signal quality for a speech portion of the received sound signal, any other suitable parameter related to the speech portion of the sound signal, or any combination thereof. If the speech signal is to be used to identify patient distress, processing may continue to step 504. If the speech signal is not to be used to identify patient distress, processing may continue to step 510.

At step 504, processor 62 may recognize speech from the sound signal. In some embodiments, words and phrases may be identified based on training data from a patient, for example, based on the patient speaking a number of predetermined words or phrases to assist in identifying patterns in the patient's speech. In some embodiments, the language spoken by the patient may be identified based on the training routine, a menu selection, any other suitable method, or any combination thereof. Although speech recognition may be performed in ay suitable manner, in some embodiments, speech may be recognized based on Hidden Markov Models, neural networks, any other suitable speech recognition method, or any combination thereof.

At step 506, processor 62 may compare the recognized speech to one or more commands. Although the recognized speech may be compared to the commands in any suitable manner, in some embodiments, the comparison may be based on predetermined words or phrases, natural language, any other suitable comparison technique, or any combination thereof. Any suitable set of commands may by identified by the comparison, such as commands related to patient distress (including requests for medication and requests for attention from a medical professional), commands for adjusting conditions within the patient treatment area, any other suitable commands, or any combination thereof.

Although any suitable commands directly indicating patient distress may be identified in any suitable manner, in some embodiments, a patient may indicate the source of the distress (e.g., physical pain, difficulty breathing, numbness, anxiety, chest pain, any other suitable source of distress, or any combination thereof), the severity level of the patient distress, requests for medication, requests for attention from a medical professional, any other suitable indication regarding the patient distress, or any combination thereof.

Although any suitable commands relating to requests for medication may be identified in any suitable manner, in some embodiments, a patient may indicate a desired medication by name, medication type, symptoms, any other suitable manner of indicating a medication, or any combination thereof.

Although any suitable commands relating to requests for attention from a medical professional may be identified in any suitable manner, in some embodiments, a patient may indicate the name of a particular medical professional, a general request for medical attention, an indication that medical supplies are in low supply, any other suitable request for attention from a medical professional, or any combination thereof.

Although any suitable commands for adjusting conditions within the patient treatment area may be identified in any suitable manner, in some embodiments, a patient may identify an item to be adjusted (e.g., bed position, lighting, television channel, any other item, or any combination thereof), a desired adjustment, any other suitable parameter, or any combination thereof.

Once one or more commands are identified, processing may continue to step 508, where processor 62 may identify a response based on the one or more commands. Although any suitable response may be identified, in some embodiments, monitor 12 may identify an audible response, a visual response, a message to be communicated to another device, an adjustment of any functionality that is integrated within monitor 12, any other suitable parameter, or any combination thereof, based on the commands identified at step 506. As is described herein, the particular response or responses may be provided by monitor 12 at step 526.

At step 510, processor 62 may determine whether to use sounds to identify patient distress. Although the determination of whether to use sounds may be performed in any suitable manner, in some embodiments, the determination may be based on the settings for monitoring unit 12, a signal quality for a portion of the received sound signal (e.g., a relevant frequency range associated with sounds of interest), any other suitable parameter related to the sounds to be identified, or any combination thereof. If patient sounds are to be used to identify patient distress, processing may continue to step 512. If patient sounds are not to be used to identify patient distress, processing may continue to step 518.

At step 512, processor 62 may identify candidate sound portions from the sound signal for further analysis. In some embodiments, sounds may be identified based on pitch, frequency, sound level, duration, periodicity, rate of change, any other suitable parameter, or any combination thereof. For example, it may be recognized that certain human sounds are associated with patient distress, such as groans, screams, sharp intakes of breath, and abrupt changes in pitch, breathing patterns, and sound level. In some embodiments, portions of the sound signal including sound patterns that are likely to conform to these conditions may be identified as candidate sound portions by processor 62. Although candidate sound portions may be identified from any suitable sound patterns, in some embodiments, the sound pattern may be based on thresholds (e.g., a pitch, frequency, or sound level threshold), sound patterns over time (e.g., changes in pitch, frequency, or sound level), any other suitable sound pattern, or any combination thereof. In some embodiments, a pitch threshold may be set at a suitable value, such that if the pitch threshold is exceeded a candidate portion may be identified as corresponding to patient distress based on the high pitch of the sound of the patient. In some embodiments, a frequency of breathing rate threshold may be set at a suitable value, such that if the frequency threshold is exceeded (e.g., based on a patient taking short, frequent breaths) a candidate portion may be identified as corresponding to patient distress. In some embodiments, a sound level threshold may be set at a suitable value, such that if the sound level threshold is exceeded (e.g., based on a patient screaming or groaning) a candidate portion may be identified as corresponding to patient distress.

At step 514, processor 62 may compare the candidate portions to one or more sound profiles. In some embodiments, a sound profile may be based at least in part on measured sounds of a patient, for example, based on a training routine. The sound profile (whether or not based on a training routine) may be based on known sound patterns that are indicative of different types and degrees of patient distress, for example, to identify patient distress, a need for medication or treatment, a need for attention from a medical professional, any other suitable patient needs, or any combination thereof.

In some embodiments, the comparison of the candidate sound portion with the sound profile may indicate the source of the distress (e.g., physical pain, difficulty breathing, numbness, anxiety, chest pain, any other suitable source of distress, or any combination thereof), the severity level of the patient distress, any other suitable indication regarding the patient distress, or any combination thereof. In some embodiments, the comparison of the candidate sound portion with the sound profile may indicate need for medication, treatment, or a medical professional.

Once the candidate sound portion is compared to the sound profile, processing may continue to step 516, where processor 62 may identify a response based on the one or more commands. Although any suitable response may be identified, in some embodiments, monitor 12 may identify an audible response, a visual response, a message to be communicated to another device, an adjustment of any functionality that is integrated within monitor 12, any other suitable parameter, or any combination thereof, based on output of step 514. As is described herein, the particular response or responses may be provided by monitor 12 at step 526.

At step 518, processor 62 may determine whether to use a classifier to identify patient distress. Although the determination of whether to use a classifier may be performed in any suitable manner, in some embodiments, the determination may be based on the settings for monitoring unit 12, a signal quality for a portion of the received sound signal (e.g., a relevant frequency range associated with sounds of interest), any other suitable parameter related to the received sound signal, or any combination thereof. If a classifier is to be used to identify patient distress, processing may continue to step 520. If a classifier is not to be used to identify patient distress, processing may continue to step 526.

At step 520, processor 62 may calculate metrics to be input to the classifier. As described herein, the classifier may be trained based on training data. Metrics may be measurements that conform to the training data, and may be based on patient sounds, patterns of patient sounds, speech commands, patterns of speech commands, any other suitable measurement related to the patient sound signal, or any combination thereof. It will be understood that any suitable number of metrics may be calculated from the received sound signal (or any data or signal obtained from the received sound signal), and that any number of metrics or combinations thereof may be input to any number of classifiers, for example, to identify different conditions indicative of patient distress. Examples of metrics include the frequency (pitch) of the sound(s), changes in the frequency (or tone) which may be used to inflect sound or speech patterns to convey emotional meaning, the amplitude (volume) and the change in amplitude of the signal which may indicate pain or stress, the appearance and disappearance of certain frequencies, ratios of the amplitudes of certain frequencies, the timbre (rise, duration and decay) of the sound signal components, or any other suitable metrics. These metrics may be computed from information extracted from the signal using a number of techniques. In some embodiments, the amplitude and frequency components of the signal may be extracted from the signal itself, or from the transform of a signal, including a Fourier or wavelet transform. In some embodiments, the metrics may be compared to a threshold which when exceeded may indicate patient distress. In some embodiments, the metrics may be input into a classifier which may have previously been trained on historic data. The classifier may use these metrics to indicate patient distress as described herein.

At step 522, processor 62 may process the metrics with one or more classifiers. As described herein, any suitable classifier may be used in accordance with the present disclosure, such as neural networks (e.g., MPL networks or radial basis networks), genetic algorithms, stochastic and probabilistic classifiers (e.g., Basian, HMM, or fuzzy classifiers), propositional or predicate logics (e.g., non-monotonic or modal logics), nearest neighbor classification methods (e.g., $k^{th}$ nearest neighbor or LVQ methods), any other suitable classifiers, or any combination thereof. Although any suitable signal processing techniques may be employed by the classifiers, exemplary signal processing techniques may include PCA, ICA, LDA, fast Fourier transforms, continuous wavelet transforms, Hilbert transforms, Laplace transforms, any other suitable signal processing method, or any combination thereof.

In some embodiments, each classifier may output one or more values indicative of patient distress (including a need for medication or a need for attention from a medical professional), any other suitable values, or any combination thereof. In some embodiments, one or more of the classifiers may output logical values (e.g., "1" or "0") indicative of the presence of patient distress, severity values indicative of the presence and severity of patient distress, any other suitable value relating to patient distress, or any combination thereof.

Although a classifier output directly indicative of patient distress may provide any suitable information, in some embodiments, the classifier output may indicate the source of the distress (e.g., physical pain, difficulty breathing, numbness, anxiety, chest pain, any other suitable source of distress, or any combination thereof), the severity level of the patient distress, any other suitable indication regarding the patient distress, or any combination thereof.

Although a classifier output indicative of a patient need for medication may identify any suitable information relating to medication needs, in some embodiments, the classifier output may indicate a medication type, medication dosage, any other information relating to medication, or any combination thereof.

Although a classifier output indicative of a need for attention from a medical professional may identify any suitable information, in some embodiments, the classifier output may indicate a particular medical professional, a general request for medical attention, an indication that medical supplies are in low supply, any other suitable indication relating to the need for medical attention, or any combination thereof.

Once the outputs of the one or more classifiers have been determined, processing may continue to step 524, where processor 62 may identify a response based on the one or more commands. Although any suitable response may be identified, in some embodiments, monitor 12 may identify an audible response, a visual response, a message to be communicated to another device, an adjustment of any functionality that is integrated within monitor 12, any other suitable parameter, or any combination thereof, based on output of step 514. As is described herein, the particular response or responses may be provided by monitor 12 at step 526.

At step 526 monitor 12 may provide a response or set of responses based on the identified responses from one or more of steps 508, 516, or 524. In some embodiments, monitor 12 may sound an alarm from speaker 16, provide an audible message from speaker 16, indicate an alarm on display 14, provide a message on display 14, communicate with external devices via communication unit 24, or adjust treatments or parameters that are integrated within monitor 12.

In some embodiments, speaker 16 may provide an alarm based on the response identified at one or more of steps 508, 516, and 524. Although alarms may be provided in any suitable manner, in some embodiments, the tone, duration, sound level, any other suitable parameter, or any combination thereof, may be selected based on the type of response. For example, the parameters of the alarm may be selected in a different manner for different indications of distress or different severities.

In some embodiments, speaker 16 may provide an audible message based on the response identified at one or more of steps 508, 516, and 524. Although audible messages may be provided in any suitable manner, in some embodiments, an audible message may be selected from one or more predetermined messages, for example to indicate the presence of patient distress, the severity of patient distress, a need for medication or treatment, a request for attention from a medical professional, any other suitable parameter, or any combination thereof.

In some embodiments, an alarm may be indicated on display 14 based on the response identified at one or more of steps 508, 516, and 524. Although an alarm may be displayed in any suitable manner, in some embodiments, an alarm type (e.g., patient distress, medication needed, medical attention needed, any other suitable alarm type, or any combination thereof) and severity may be displayed within alarm portion 32. In some embodiments, a message may be indicated on display 14 based on the response identified at one or more of steps 508, 516, and 524, for example, within menu portion 22.

In some embodiments, monitor 12 may communicate with external devices via communication unit 24 based on the response identified at one or more of steps 508, 516, and 524. Although monitor 12 may communicate with any suitable devices, in some embodiments, monitor 12 may communicate with nurse stations, central monitoring stations, remote servers, pagers, mobile telephones, medical devices, any other suitable device, or any combination thereof. For example, in an embodiment, in response to an indication of severe patient distress, monitoring unit 12 may communicate a message to a central monitoring station and to a pager of an attending physician, and may send a message to a device for dispensing pain medication that enables the pain medication to be delivered to a patient. It will also be understood that any other suitable functionality may be integrated with monitor 12, such that in some embodiments, the integrated functionality of monitor 12 may directly perform the functionality in response to an indication of patient distress (e.g., delivery of medication).

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method comprising:
   receiving a sound signal from a sensor that senses sound from a patient, the sound signal indicative of human non-speech vocalization;
   computing, with processing equipment, one or more metrics based on the sound signal;
   determining, with the processing equipment, a classification of the sound signal based on the one or more metrics and on a classifier, wherein the classifier is trained based on signal characteristics that correspond to patient distress;
   determining, with the processing equipment, whether the sound signal corresponds to patient distress based on the classification; and
   outputting an indication of patient distress when patient distress is determined to be present.

2. The method of claim 1, further comprising:
   recognizing speech based on the sound signal;
   determining a command based on the recognized speech; and
   further determining whether the sound signal corresponds to patient distress based on the command.

3. The method of claim 2, wherein the command comprises one or more of a request for assistance, an indication of pain level, and a request for medication.

4. The method of claim 1, further comprising:
   identifying a candidate portion of the sound signal; and
   further determining whether the sound signal corresponds to patient distress based on the candidate portion.

5. The method of claim 4, wherein the candidate portion is identified based on one or more of a sound level, pitch, frequency, a rate of change of the sound level, a rate of change of the pitch, and a rate of change of the frequency.

6. The method of claim 1, wherein the classifier comprises one or more of a neural network, a genetic algorithm, stochastic classifiers, probabilistic classifiers, propositional logics, predicate logics, and nearest neighbor classification methods.

7. The method of claim 1, further comprising:
   processing the sound signal to generate a respiration signal; and
   determining respiration information based on the respiration signal.

8. A non-transitory computer-readable storage medium for processing a sound signal, the computer-readable medium having computer program instructions recorded thereon for:
   receiving a sound signal from a sensor that senses sound from a patient, the sound signal indicative of human non-speech vocalization;
   computing one or more metrics based on the sound signal;
   determining a classification of the sound signal based on the one or more metrics and on a classifier, wherein the classifier is trained based on signal characteristics that correspond to patient distress;
   determining whether the sound signal corresponds to patient distress based on the classification; and
   outputting an indication of patient distress when patient distress is determined to be present.

9. The computer-readable medium of claim 8, the computer-readable medium having computer program instructions recorded thereon for:
   recognizing speech based on the sound signal;
   determining a command based on the recognized speech; and
   further determining whether the sound signal corresponds to patient distress based on the command.

10. The computer-readable medium of claim 9, wherein the command comprises one or more of a request for assistance, an indication of pain level, and a request for medication.

11. The computer-readable medium of claim 8, the computer-readable medium having computer program instructions recorded thereon for:
    identifying a candidate portion of the sound signal; and
    further determining whether the sound signal corresponds to patient distress based on the candidate portion.

12. The computer-readable medium of claim 11, wherein the candidate portion is identified based on one or more of a sound level, pitch, frequency, a rate of change of the sound level, a rate of change of the pitch, and a rate of change of the frequency.

13. The computer-readable medium of claim 8, wherein the classifier comprises one or more of a neural network, a genetic algorithm, stochastic classifiers, probabilistic classifiers, propositional logics, predicate logics, and nearest neighbor classification methods.

14. A monitoring unit comprises processing equipment configured to:
    receive a sound signal from a sensor that senses sound from a patient, the sound signal indicative of human non-speech vocalization;

compute one or more metrics based on the sound signal;

determine a classification of the sound signal based on the one or more metrics and on a classifier, wherein the classifier is trained based on signal characteristics that correspond to patient distress;

determine whether the sound signal corresponds to patient distress based on the classification; and output an indication of patient distress when patient distress is determined to be present.

15. The monitoring unit of claim 14, wherein the monitoring unit is further configured to:

recognize speech based on the sound signal;

determine a command based on the recognized speech; and further determine whether the sound signal corresponds to patient distress based on the command.

16. The monitoring unit of claim 15, wherein the command comprises one or more of a request for assistance, an indication of pain level, and a request for medication.

17. The monitoring unit of claim 14, wherein the monitoring unit is further configured to:

identify a candidate portion of the sound signal; and further determine whether the sound signal corresponds to patient distress based on the candidate portion.

18. The monitoring unit of claim 17, wherein the candidate portion is identified based on one or more of a sound level, pitch, frequency, a rate of change of the sound level, a rate of change of the pitch, and a rate of change of the frequency.

19. The monitoring unit of claim 14, wherein the monitoring unit is further configured to:

process the sound signal to generate a respiration signal;

determine respiration information based on the respiration signal.

20. The monitoring unit of claim 14, wherein the classifier comprises one or more of a neural network, a genetic algorithm, stochastic classifiers, probabilistic classifiers, propositional logics, predicate logics, and nearest neighbor classification methods.

* * * * *